United States Patent
Nishikawa

(10) Patent No.: US 7,692,033 B2
(45) Date of Patent: Apr. 6, 2010

(54) PROCESS FOR PRODUCING 2-BENZOYLOXYACETALDEHYDE DERIVATIVE

(75) Inventor: Kazuyoshi Nishikawa, Tsukuba (JP)

(73) Assignee: Daicel Chemical Industries, Ltd., Osaka (JP)

( * ) Notice: Subject to any disclaimer, the term of this patent is extended or adjusted under 35 U.S.C. 154(b) by 1324 days.

(21) Appl. No.: 11/076,900

(22) Filed: Mar. 11, 2005

(65) Prior Publication Data

US 2005/0234246 A1    Oct. 20, 2005

(30) Foreign Application Priority Data

Apr. 19, 2004    (JP) .............................. 2004-123469

(51) Int. Cl.
C07C 69/74 (2006.01)
C07C 69/66 (2006.01)
(52) U.S. Cl. ...................................... 560/126; 560/187
(58) Field of Classification Search ................. 560/126, 560/187; 549/39
See application file for complete search history.

(56) References Cited

FOREIGN PATENT DOCUMENTS

WO    WO-03/051298 A2    6/2003

OTHER PUBLICATIONS

Nebergall et al, College Chemistry with qualitative analysis, p. 89, 1980.*
J. Org. Chem., vol. 42, No. 17, 1977, "1,2-Bis(2-hydroxyethyl)hydrazine and Derivatives1", pp. 2900-2902.
Bioorganic & Medicinal Chemistry, vol. 4, No. 12, "Synthesis, NMR Spectroscopy Study, and Antimuscarinic Activity of a Series of 2-(Acyloxymethyl)-1,3-dioxolanes", pp. 2071-2080 (1996).

* cited by examiner

Primary Examiner—Taylor Victor Oh
(74) Attorney, Agent, or Firm—Birch, Stewart, Kolasch & Birch LLP

(57) ABSTRACT

A process produces a 2-benzoyloxyacetaldehyde derivative represented by following Formula (3):

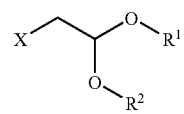

(3)

wherein $R^1$ and $R^2$ may be the same as or different from each other and are each a hydrocarbon group, wherein $R^1$ and $R^2$ may be combined to form a ring with the adjacent oxygen-carbon-oxygen bond, and wherein the benzene ring in the formula may be substituted, by allowing a halogenated acetaldehyde acetal derivative represented by following Formula (1):

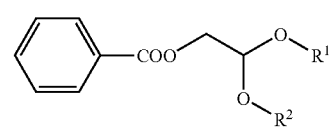

(1)

wherein $R^1$ and $R^2$ are as defined above; and X represents a halogen atom, to react with a benzoate represented by following Formula (2):

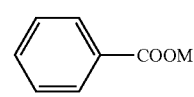

(2)

wherein M represents an alkali metal atom and wherein the benzene ring in the formula may be substituted, in the presence of an alkali-metal halide.

5 Claims, No Drawings

PROCESS FOR PRODUCING 2-BENZOYLOXYACETALDEHYDE DERIVATIVE

BACKGROUND OF THE INVENTION

1. Field of the Invention

The present invention relates to a process for producing 2-benzoyloxyacetaldehyde derivatives that are useful as fine chemicals such as pharmaceutical preparations and agricultural chemicals and as intermediates thereof.

2. Description of the Related Art

A process for producing a 2-benzoyloxyacetaldehyde derivative has been reported in J. Org. Chem. 1977, 42, 2900-2902. This process comprises the steps of converting chloroacetaldehyde diethyl acetal into 2-hydroxyacetaldehyde diethyl acetal by treating with an aqueous potassium hydroxide solution at high temperatures under pressure (under a load), and converting the resulting compound into 2-benzoyloxyacetaldehyde diethyl acetal by treating with benzoyl chloride. The process, however, cannot be said as an industrially advantageous process, since the first step of converting the chlorine substituent into hydroxyl group requires pressurization, the high-yield isolation of resulting 2-hydroxyacetaldehyde diethyl acetal requires complicated procedures, and the preparation of the target compound from the starting material, chloroacetaldehyde diethyl acetal, requires two stage reactions including conversion of the chlorine substituent into hydroxyl group, and condensation with benzoyl chloride.

Bioorg. Med. Chem., 1996, 2071-2080 and PCT International Publication Number WO 03/051298 disclose a process for preparing a 2-benzoyloxyacetaldehyde derivative by allowing a halogenated acetaldehyde dimethyl acetal to react with potassium benzoate in the presence of dichlorohexyl-18-crown-6-ether. This process can yield the target compound under normal pressure in one step, is more advantageous than the above-mentioned process, but is still not industrially advantageous, because dichlorohexyl-18-crown-6-ether for use in the reaction is hardly available. In addition, according to the process, the condensation between a benzoate and a chloroacetaldehyde acetal derivative yields the target compound only in a low yield, although the condensation between the benzoate and a bromoacetaldehyde acetal derivative proceeds relatively smoothly.

SUMMARY OF THE INVENTION

Accordingly, an object of the present invention is to provide a process for efficiently producing a 2-benzoyloxyacetaldehyde derivative with the use of a raw material that is industrially easily available.

After intensive investigations to achieve the above object, the present inventors have found that a 2-benzoyloxyacetaldehyde derivative can be efficiently produced by incorporating an alkali-metal halide to the reaction between a halogenated acetaldehyde acetal derivative and a benzoate, and that a 2-benzoyloxyacetaldehyde derivative having a sulfur-oxygen-containing heterocycle can be easily prepared by allowing the above-mentioned product to react with a hydroxymercaptan compound in the presence of an acid catalyst to thereby proceed the transacetalation smoothly. The present invention has been accomplished based on these findings.

Specifically, the present invention provides, in an aspect, a process for producing a 2-benzoyloxyacetaldehyde derivative represented by following Formula (3):

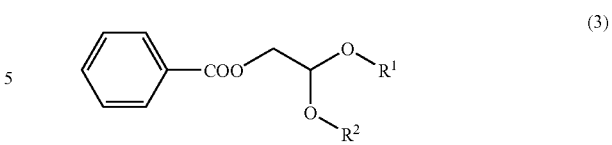

wherein $R^1$ and $R^2$ may be the same as or different from each other and are each a hydrocarbon group, wherein $R^1$ and $R^2$ may be combined to form a ring with the adjacent oxygen-carbon-oxygen bond, and wherein the benzene ring in the formula may be substituted, the process including the step of:

allowing a halogenated acetaldehyde acetal derivative represented by following Formula (1):

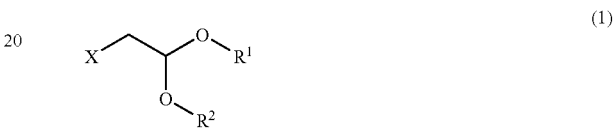

wherein $R^1$ and $R^2$ are as defined above; and X represents a halogen atom, to react with a benzoate represented by following Formula (2):

wherein M represents an alkali metal atom and wherein the benzene ring in the formula may be substituted, in the presence of an alkali-metal halide.

In the process, it is preferred that X in Formula (1) is chlorine atom and that the alkali-metal halide is potassium iodide. The halogenated acetaldehyde acetal derivative represented by Formula (1) is preferably chloroacetaldehyde dimethyl acetal or chloroacetaldehyde diethyl acetal. Potassium benzoate is advantageously used as the benzoate represented by Formula (2).

The present invention provides, in another aspect, process for producing a 2-benzoyloxyacetaldehyde derivative represented by following Formula (5):

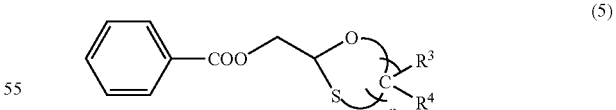

wherein $R^3$ and $R^4$ may be the same as or different from each other and are each hydrogen atom or a hydrocarbon group; and n represents 2 or 3, wherein $nR^3s$ and $nR^4S$ may be the same as or different from each other, respectively, wherein $R^3$ with $R^4$, $R^3$s bound to different carbon atoms, and/or $R^4$s bound to different carbon atoms, respectively, may be combined to form a ring with the adjacent carbon atom or carbon-carbon bond, and wherein the benzene ring in the formula may be substituted, the process including the steps of:

preparing a compound represented by following Formula (3):

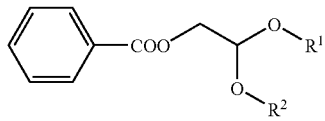

(3)

wherein $R^1$ and $R^2$ may be the same as or different from each other and are each a hydrocarbon group, wherein $R^1$ and $R^2$ may be combined to form a ring with the adjacent oxygen-carbon-oxygen bond, and wherein the benzene ring in the formula may be substituted, by the above-mentioned process;

allowing the compound represented by Formula (3) to react with a hydroxymercaptan compound represented by following Formula (4):

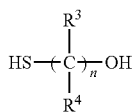

(4)

wherein $R^3$, $R^4$ and n are as defined above, in the presence of an acid catalyst.

The present invention can industrially efficiently produce 2-benzoyloxyacetaldehyde derivatives with the use of easily available raw materials.

Further objects, features and advantages of the present invention will become apparent from the following description of the preferred embodiments.

DESCRIPTION OF THE PREFERRED EMBODIMENTS

In the halogenated acetaldehyde acetal derivative of Formula (1), the hydrocarbon groups in $R^1$ and $R^2$ include, for example, aliphatic hydrocarbon groups, alicyclic hydrocarbon groups, aromatic hydrocarbon groups, and groups each comprising two or more of these groups bound to each other. Examples of the aliphatic hydrocarbon groups are linear or branched-chain alkyl groups including alkyl groups each having one to six carbon atoms, such as methyl group, ethyl group, propyl group, isopropyl group, butyl group, isobutyl group, t-butyl group, pentyl group and hexyl group; alkenyl groups including alkenyl groups each having two to six carbon atoms, such as vinyl group and allyl group; and alkynyl groups including alkynyl groups each having two to six carbon atoms, such as propynyl group. Examples of the alicyclic hydrocarbon groups are cycloalkyl groups including cycloalkyl groups each having three to eight carbon atoms, such as cyclopropyl group, cyclopentyl group and cyclohexyl group. Examples of the aromatic hydrocarbon groups are aryl groups including aryl groups each having six to fourteen carbon atoms, such as phenyl group and naphthyl group. Examples of groups each comprising an aliphatic hydrocarbon group and an aromatic hydrocarbon group bound to each other are aralkyl groups such as benzyl group and 2-phenylethyl group. Each of these hydrocarbon groups may have one or more substituents. The substituents are not specifically limited, as long as they do not adversely affect the reaction with the compound of Formula (2).

$R^1$ and $R^2$ may be combined to form a ring with the adjacent oxygen-carbon-oxygen bond. Examples of the ring are 1,3-dioxetane ring, 1,3-dioxolane ring, 1,3-dioxane ring, 1,3-dioxepane ring and 1,3-dioxocane ring.

Each of $R^1$ and $R^2$ is preferably an alkyl group having one to six carbon atoms or an aryl group, of which methyl group or ethyl group is more preferred.

The halogen atom as X includes, for example, chlorine, bromine and iodine atoms, of which chlorine atom is most preferred for better results.

Typical examples of the halogenated acetaldehyde acetal derivative of Formula (1) are compounds wherein X is chlorine atom, such as chloroacetaldehyde dimethyl acetal, chloroacetaldehyde diethyl acetal, chloroacetaldehyde dipropyl acetal and chloroacetaldehyde diisopropyl acetal; compounds wherein X is bromine atom, such as bromoacetaldehyde dimethyl acetal and bromoacetaldehyde diethyl acetal; and compounds wherein X is iodine atom, such as iodoacetaldehyde dimethyl acetal. Among them, compounds wherein X is chlorine atom, such as chloroacetaldehyde dimethyl acetal and chloroacetaldehyde diethyl acetal, are preferred.

Examples of the alkali metal atom represented by M in the benzoate of Formula (2) are lithium, sodium, potassium and cesium, of which potassium is specifically preferred.

The benzene ring in the benzoate of Formula (2) may have one to five substituents. The substituents are not specifically limited, as long as they do not adversely affect the reaction with the compound of Formula (1), and typical examples thereof are linear or branched-chain alkyl groups including alkyl groups each having one to six carbon atoms, such as methyl group, ethyl group, propyl group, isopropyl group, butyl group, isobutyl group, t-butyl group, pentyl group and hexyl group; alkenyl groups including alkenyl groups each having two to six carbon atoms, such as vinyl group and allyl group; alkynyl groups including alkynyl groups each having two to six carbon atoms, such as propynyl group; cycloalkyl groups including cycloalkyl groups each having three to eight carbon atoms, such as cyclopropyl group, cyclopentyl group and cyclohexyl group; aryl groups such as phenyl group and naphthyl group; aralkyl groups such as benzyl group; haloalkyl groups including haloalkyl groups each having one to six carbon atoms, such as trifluoromethyl group; halogen atoms such as fluorine atom, chlorine atom, bromine atom and iodine atom; alkoxy groups including alkoxy groups each having one to six carbon atoms, such as methoxy group and ethoxy group; acyl groups including acyl groups each having one to ten carbon atoms, such as acetyl group; alkoxycarbonyl groups including $C_1$-$C_6$ alkoxy-carbonyl groups, such as methoxycarbonyl group and ethoxycarbonyl group; cyano group; nitro group; and dialkylamino groups including di-$C_1$-$C_6$ alkyl-amino groups, such as dimethylamino group. When two or more substituents are bound on the benzene ring, they may be combined to form a ring with a carbon-carbon bond constituting the benzene ring. Preferred examples of the substituents are alkyl groups each having one to six carbon atoms, and halogen atoms.

The benzoate of Formula (2) can be prepared in the reaction system by allowing benzoic acid or a derivative thereof to react with a base containing an alkali metal in the reaction system. Examples of the base containing an alkali metal are carbonates of alkali metals, such as potassium carbonate and sodium carbonate; hydrogen carbonates of alkali metals, such as sodium hydrogen carbonate; and hydroxides of alkali metals, such as sodium hydroxide.

Typical examples of the benzoate of Formula (2) are lithium benzoate, potassium benzoate, sodium benzoate and cesium benzoate, of which potassium benzoate is preferred.

The alkali-metal halide for use in the present invention can be any alkali-metal halide and includes, for example, iodides such as potassium iodide, sodium iodide and cesium iodide; bromides such as potassium bromide, sodium bromide and cesium bromide; and chlorides such as potassium chloride. Among them, iodides are preferred, of which potassium iodide is specifically preferred.

The reaction (condensation) between the halogenated acetaldehyde acetal derivative of Formula (1) and the benzoate of Formula (2) is generally carried out in an organic solvent. The organic solvent can be any suitable one and includes, for example, aromatic hydrocarbons such as benzene, toluene and xylenes; ethers such as dioxane and tetrahydrofuran; aliphatic or alicyclic hydrocarbons such as octane, cyclohexane and cyclooctane; and aprotic polar solvents such as dimethylformamide, dimethylacetamide and dimethyl sulfoxide.

The amount of the compound of Formula (2) can be freely set, as long as the reaction is not adversely affected, and is generally from about 0.7 to 1.3 moles, and preferably from about 0.85 to 1.2 moles, per 1 mole of the compound of Formula (1).

The amount of the alkali-metal halide is generally about 1 percent by weight or more (e.g., from about 1 to about 40 percent by weight), preferably about 5 percent by weight or more (e.g., from about 5 to about 30 percent by weight), and more preferably from about 10 to about 20 percent by weight relative to the compound of Formula (1).

The condensation reaction in the present invention efficiently proceeds with heating at 80° C. or higher, for example from about 80° C. to about 250° C., and preferably at 130° C. or higher, for example from about 130° C. to about 250° C. The reaction can further be accelerated by carrying out under pressure (under a load). The reaction temperature and pressure are, however, not specifically limited.

The reaction time of the condensation varies depending typically on the type and amount of the benzoate, the type and amount of the alkali-metal halide, and the reaction temperature and is not specifically limited. The reaction can be finished generally within several hours to several ten hours.

The 2-benzoyloxyacetaldehyde derivative of Formula (3) can be obtained by extracting the product from the reaction mixture after the completion of the reaction, and subjecting the product to a conventional separation and purification means such as distillation and/or column chromatography.

The resulting 2-benzoyloxyacetaldehyde derivative of Formula (3) can be converted into the compound of Formula (5) having a sulfur-oxygen-containing heterocycle as a transacetalation product by the reaction with the hydroxymercaptan compound of Formula (4) in the presence of an acid catalyst.

Examples of the hydrocarbon groups in $R^3$ and $R^4$ in Formula (4) are the hydrocarbon groups listed in $R^1$ and $R^2$. $R^3$ with $R^4$, $R^3$s bound to different carbon atoms, and/or $R^4$s bound to different carbon atoms, respectively, may be combined to form a ring with the adjacent carbon atom or carbon-carbon bond. Examples of the ring herein are alicyclic carbon rings including cycloalkane rings (e.g., cycloalkane rings each having three to six members), such as cyclopropane ring, cyclobutane ring, cyclopentane ring and cyclohexane ring; aromatic hydrocarbon rings such as benzene ring; and aromatic or nonaromatic heterocycles including heterocycles each having three to six members, such as tetrahydrofuran ring, pyrrole ring and pyridine ring. Each of these rings may have one or more substituents.

$R^3$ and $R^4$ are each preferably hydrogen atom or an alkyl group having one to six carbon atoms. Of such alkyl groups each having one to six carbon atoms, methyl group or ethyl group is typically preferred.

Typical examples of the compound of Formula (4) are 2-mercaptoethanol, 3-mercaptopropanol, 2-mercaptopropanol, 3-mercapto-2-propanol, o-mercaptophenyl and 2-mercapto-1-cyclohexanol.

The acid catalyst can be any suitable one selected from, for example, those generally used for transacetalation including inorganic acids such as hydrochloric acid, sulfuric acid and phosphoric acid; sulfonic acids such as methanesulfonic acid, trifluoromethanesulfonic acid, benzenesulfonic acid, p-toluenesulfonic acid and naphthalenesulfonic acid; carboxylic acids such as trifluoroacetic acid; strongly acidic cation exchange resins; and solid acid catalysts.

The reaction between the compound of Formula (3) and the compound of Formula (4) is generally carried out in an organic solvent. The organic solvent is not specifically limited and includes, for example, aromatic hydrocarbons such as benzene, toluene and xylenes; ethers such as dioxane and tetrahydrofuran; aliphatic or alicyclic hydrocarbons such as octane, cyclohexane and cyclooctane; and aprotic polar solvents such as dimethylformamide, dimethylacetamide and dimethyl sulfoxide.

The amount of the compound of Formula (4) can be freely set within a range not deteriorating the reaction and is generally from about 0.7 to about 1.3 moles, and preferably from about 0.85 to about 1.2 moles per 1 mole of the compound of Formula (3).

The amount of the acid catalyst is generally from about 0.01 to about 20 percent by weight, preferably from about 0.1 to about 10 percent by weight, and more preferably from about 0.5 to about 5 percent by weight, relative to the compound of Formula (3).

The reaction temperature varies depending typically on the types of the reaction components and is generally from about 10° C. to about 250° C., and preferably from about 50° C. to about 200° C. The reaction can be carried out while distilling off by-produced hydroxy compounds such as $R^1OH$ and $R^2OH$ with the solvent, for accelerating the reaction. The reaction pressure and reaction time can be appropriately set in consideration typically of the types of the reaction components, the type and amount of the acid catalyst, and operability.

The reaction produces the compound of Formula (5) in a high yield, as a result of transacetalation. For example, the use of a compound of Formula (4) wherein n is 2, such as 2-mercaptoethanol, yields a 2-benzoyloxymethyl-1,3-oxathiolane compound (five-membered heterocyclic compound). The use of a compound of Formula (4) wherein n is 3, such as 3-mercaptopropanol, yields a 2-benzoyloxymethyl-1,3-oxathiane compound (six-membered heterocyclic compound).

The reaction product after the completion of the reaction can be isolated by general separation/purification means such as extraction, distillation, crystallization, recrystallization and/or column chromatography. The above-mentioned process can industrially efficiently produce a 1,3-oxathiolane compound or 1,3-oxathiane compound having benzoyloxymethyl group bound at the 2-position (a kind of 2-benzoyloxyacetaldehyde derivatives) from easily available starting materials in a short process.

The 2-benzoyloxyacetaldehyde derivatives of Formula (3) or (5) can be used as fine chemicals such as pharmaceutical preparations and agricultural chemicals, or as intermediates thereof.

The present invention will be illustrated in further detail with reference to several examples below, which are never intended to limit the scope of the invention. NMR spectra were determined using a spectrometer Bruker AVANCE (registered trademark) 500 with tetramethylsilane (TMS) as an internal standard.

EXAMPLE 1

Preparation of 2-benzoyloxyacetaldehyde dimethyl acetal

Chloroacetaldehyde dimethyl acetal (50.0 g), potassium benzoate (70.7 g), potassium iodide (6.66 g) and DMF (N,N-dimethylformamide) (250 mL) were placed in a three-neck flask, followed by refluxing. Twenty hours later, the reaction mixture was cooled to room temperature, and water (250 mL) and ethyl acetate (250 mL) were added thereto, followed by stirring. After filtration, the filtrate was extracted with ethyl acetate (500 mL). The organic layer was subjected to vacuum concentration and then to vacuum distillation at 132-135° C. and at 5 mmHg and thereby yielded the target compound (61.0 g) in a yield of 72%.

$^1$H-NMR (CDCl$_3$) δ: 8.06 (m, 2H), 7.56 (m, 1H), 7.44 (m, 2H), 4.72 (t, 1H), 4.36 (d, 2H), 3.44 (s, 6H)

EXAMPLE 2

Preparation of 2-benzoyloxyacetaldehyde diethyl acetal

Chloroacetaldehyde diethyl acetal (2.00 g), potassium benzoate (1.91 g), potassium iodide (0.41 g) and DMF (20 mL) were placed in a three-neck flask, followed by refluxing. Twenty hours later, the reaction mixture was cooled to room temperature, and water (30 mL) and ethyl acetate (80 mL) were added thereto, followed by stirring. After filtration, the organic layer was separated, was subjected to vacuum concentration and then to Kugelrohr distillation at 110-120° C. and at 1 mmHg and thereby yielded the target compound (2.41 g) in a yield of 77%.

EXAMPLE 3

Preparation of 2-benzoyloxyacetaldehyde diethyl acetal

Chloroacetaldehyde diethyl acetal (2.00 g), potassium benzoate (1.91 g), potassium bromide (0.30 g) and DMF (20 mL) were placed in a three-neck flask, followed by refluxing. Twenty hours later, the reaction mixture was cooled to room temperature, and water (30 mL) and ethyl acetate (80 mL) were added thereto, followed by stirring. After filtration, the organic layer was washed with water (30 mL) and was dried over anhydrous sodium sulfate. Subsequent filtration and vacuum concentration yielded the target compound (0.97 g) in a yield of 31%.

EXAMPLE 4

Preparation of 2-benzoyloxyacetaldehyde diethyl acetal

Chloroacetaldehyde diethyl acetal (2.00 g), benzoic acid (2.16 g), potassium iodide (0.27 g), potassium carbonate (1.11 g) and DMF (20 mL) were placed in a three-neck flask, followed by refluxing. Twenty hours later, the reaction mixture was cooled to room temperature, and water (30 mL;) and ethyl acetate (80 mL) were added thereto, followed by stirring. After filtration, the organic layer was separated, was subjected to vacuum concentration and thereby yielded the target compound (1.74 g) in a yield of 56%.

EXAMPLE 5

Preparation of 2-benzoyloxymethyl-1,3-oxathiolane

Aliquots of 2-benzoyloxyacetaldehyde dimethyl acetal (50.0 g) prepared according to Example 1, 2-mercaptoethanol (20.4 g), p-toluenesulfonic acid monohydrate (0.90 g) and toluene (250 mL) were placed in a three-neck flask, followed by heating. By-produced methanol was distilled off with the solvent. After distilling off about 150 mL, the reaction mixture was cooled to room temperature, was washed with a saturated aqueous sodium hydrogen carbonate solution and water and was dried over anhydrous sodium carbonate. After filtration and vacuum distillation at 144-147° C. and at 0.60 mmHg, the target compound (54.9 g) was obtained in a yield of 100%.

$^1$H-NMR (CDCl$_3$) δ: 8.07 (m, 2H), 7.55 (m, 1H), 7.44 (m, 2H), 5.47 (dd, 1H), 4.43 (m, 2H), 4.29 (m, 1H), 4.01 (m, 1H), 3.06 (m, 2H)

COMPARATIVE EXAMPLE 1

Preparation of 2-benzoyloxyacetaldehyde diethyl acetal

Chloroacetaldehyde diethyl acetal (1.9 g), potassium benzoate (2.0 g) and DMF (20 mL) were placed in a three-neck flask, followed by refluxing. Twenty hours later, the reaction mixture was cooled to room temperature, and water (60 mL) and ethyl acetate (80 mL) were added thereto, followed by stirring. After filtration and separation, the organic layer was concentrated and thereby yielded the target compound (0.69 g) in a yield of 30%.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A process for producing a 2-benzoyloxyacetaldehyde compound represented by the following Formula (3):

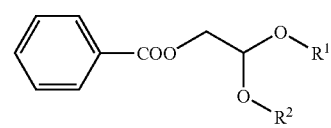

(3)

wherein $R^1$ and $R^2$ may be the same as or different from each other and are each an aliphatic hydrocarbon group having from 1 to 6 carbon atoms, an alicyclic hydrocarbon group having 3 to 8 carbon atoms, an aromatic hydrocarbon group having 6 to 14 carbon atoms, an alkenyl group having 2 to 6 carbon atoms, an alkynyl group having 2 to 6 carbon atoms, or an aralkyl group having, the aliphatic hydrocarbon group and aromatic hydrocarbon group being bound to each other to form the aralkyl group, and wherein $R^1$ and $R^2$ may be combined to form a ring with the adjacent oxygen-carbon-oxygen bond, and wherein the benzene ring in the formula may be substituted, the process comprising the step of allowing a halogenated acetaldehyde acetal compound represented by the following Formula (1):

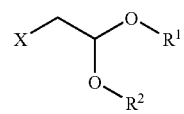

(1)

wherein $R^1$ and $R^2$ are as defined above; and X represents a halogen atom, to react with a benzoate represented by the following Formula (2):

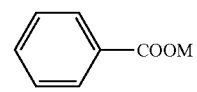

(2)

wherein M represents an alkali metal atom and wherein the benzene ring in the formula may be substituted, in the presence throughout the whole reaction of an alkali-metal halide, wherein the amount of the alkali-metal halide is 1 percent by weight or more based on the amount of the compound of Formula (1).

2. The process according to claim 1, wherein X in Formula (1) is a chlorine atom, and wherein the alkali-metal halide is potassium iodide.

3. The process according to one of claims 1 and 2, wherein the halogenated acetaldehyde acetal compound represented by Formula (1) is one of chloroacetaldehyde dimethyl acetal and chloroacetaldehyde diethyl acetal.

4. The process according to claim 1, wherein the benzoate represented by Formula (2) is potassium benzoate.

5. The process according to claim 1, wherein the amount of the alkali-metal halide is 1-40 percent by weight.

* * * * *